May 20, 1969 T. HUSTON Plant Pat. 2,888
PEACH TREE
Filed Oct. 31, 1967
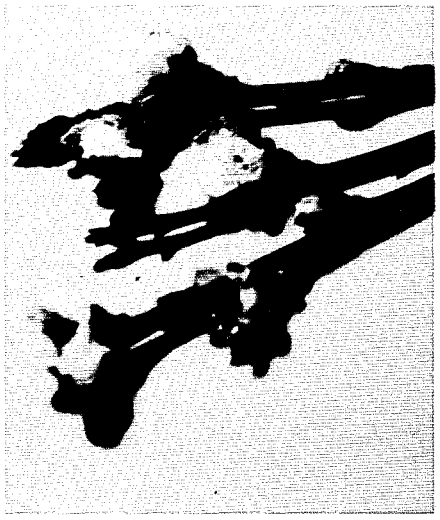
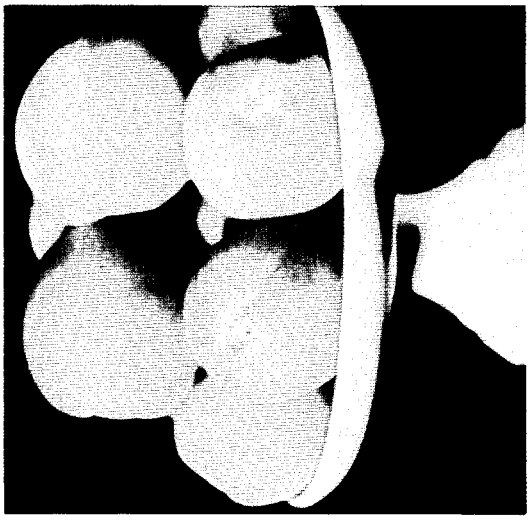
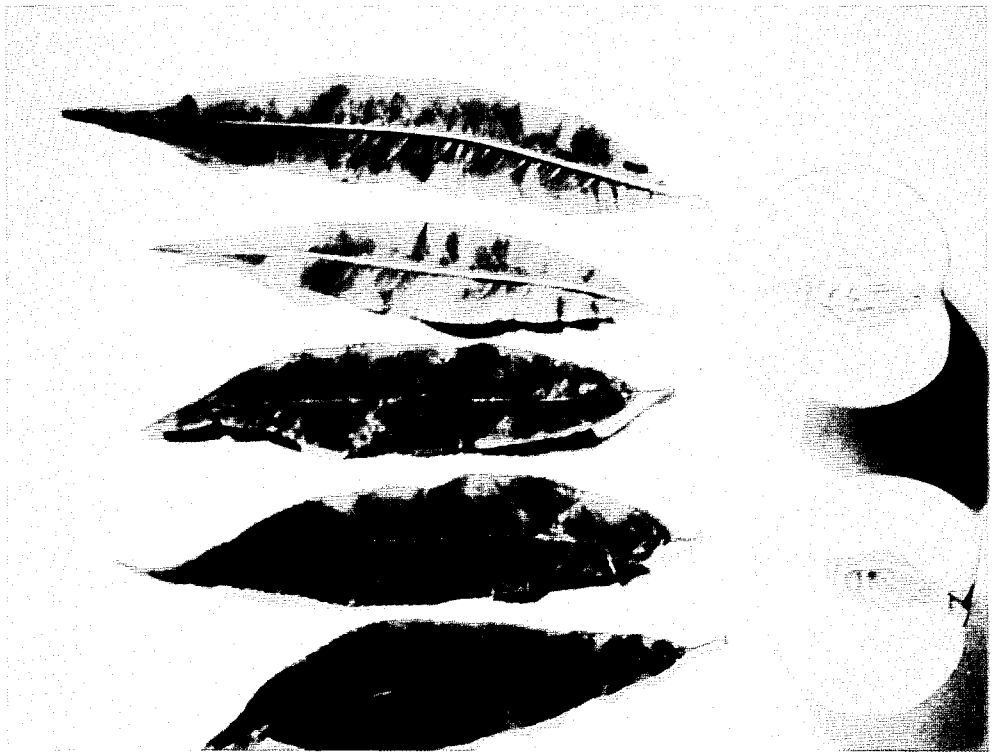
Inventor.
Tom Huston
By: Robb & Robb
Attorneys.

United States Patent Office

Plant Pat. 2,888
Patented May 20, 1969

2,888
PEACH TREE

Tom Huston, Miami, Fla., assignor to Peaches of Florida, Inc., Balm, Fla., a corporation of Florida Filed Oct. 31, 1967, Ser. No. 679,581
Int. Cl. A01h 5/08
U.S. Cl. Plt.—43 1 Claim The present invention relates to a new and distinct variety of peach tree of the yellow-fleshed, freestone fruit-bearing type, which was originated by me by crossing the variety of peach known as "Blazing Gold" (Plant Patent No. 1,127) with an unnamed and unpatented seedling of the peach variety known as "Southland" (unpatented) × an unnamed and unpatented Hawaiian F2 peach seedling.

As the result of this breeding, I have produced a new and improved variety of peach tree which is distinguished from its parents, as well as from all other peach varieties of which I am aware, as evidenced by the following characteristics which are outstanding therein:

(1) Large, showy, pink colored flowers;

(2) Good production of firm yellow-fleshed fruit of the freestone type and of relatively large size and which develops a superior red blushing of the skin;

(3) A relatively early fruit ripening habit corresponding to the very earliest of freestone varieties, while filling a void in the usual chain of ripening of established commercial varieties;

(4) A relatively low chilling requirement of about 400 to 450 hours at or below 45° F. for breaking dormancy and making the new variety adaptable to geographical areas where few peaches are grow commercially; and (5) A superior fruit quality with respect to eating, keeping and shipping qualities.

Asexual reproduction of my new variety by budding, as performed at Hawthorne, Fla., shows that the foregoing characteristics and distinctions come true to form and are established and transmitted through succeeding propagations.

The accompanying drawings show typical specimens of the foliage, partly open flowers, and fruit of my new variety, with both the upper and lower surfaces of the foliage being illustrated, as well as both exterior and sectional views of the fruit being shown, all as depicted in color as nearly true as it is reasonably possible to make the same in a color illustration of this character.

The following is a detailed description of my new variety, as based upon observations of specimens grown at Hawthorne, Fla., with color terminology in accordance with Nickerson's Color Fan, published by Munsell Color Company, Inc., of Baltimore, Md., except where general color terms of ordinary dictionary significance are obvious:

Tree: Medium size; medium vigorous; spreading; open; vase-formed; hardy; very productive; regular bearer.

*Trunk.*—Stocky; medium smooth.

*Branches.*—Stocky; medium smooth. Color—brown. Lenticels—medium number; medium size.

*Leaves.*—Medium size; lanceolate; medium thickness; smooth. Length—about 4¾ inches. Width—about 1 inch. Color: upper side—near Moderate Olive Green, Plate 7.5GY 4/4; under side—near Strong Yellow Green, Plate 7.5GY 6/8. Margin—crenate. Petiole—medium length; medium thickness. Glands—average 2 in number; opposite; medium size; uniform; basal; color—red. Stipules—2 per leaf.

Flower:

*Flower buds.*—Hardy; large; medium length; plump; free; pubescent.

*Flowers.*—Dates of first and full bloom—February 25 and March 5, respectively; late in comparison with other varieties. Size—large. Color—pink; showy.

Fruit:

*Maturity when described.*—Eating hard; June 10.

*Size.*—Variable; from medium to large. Axial diameter—from 2½ to 2¾ inches. Transverse diameter in suture plane—from 2¼ inches to 2¾ inches. Diameter at right angles to suture plane—from 2 inches to 2¼ inches.

*Form.*—Variable; some symmetrical and some unsymmetrical; broadly oblong.

*Suture.*—Distinct; shallow.

*Ventral surface.*—Rounded; lips equal.

*Cavity.*—Abrupt. Depth—¼ inch. Breadth—⅜ inch. Markings—rounded.

*Base.*—Rounded.

*Apex.*—Short. Pistil point—apical.

*Stem.*—Stout; glabrous. Length—¼ inch. Adherence to stone—medium strong.

*Skin.*—Medium thickness; medium toughness; tenacious to flesh; good blush color near Strong Red, Plate 2.5R 5/12. Tendency to crack—none in wet or dry seasons. Down—moderate abundance; medium length.

*Flesh.*—Color—near Moderate Orange Yellow, Plate 10YR 8/10, with very slight reddening at pit cavity. Amygadlin—scant. Juice—moderate abundance. Texture—firm; medium fine. Fibres—few. Ripens—evenly. Flavor—medium acid; delicate. Aroma—medium strong. Eating quality—from good to best.

*Stone.*—Free; parts smoothly from flesh. Size—from small to medium. Length—1¼ inches. Breadth—⅝ inch. Thickness—½ inch. Form—oblong. Base—straight. Apex—acute. Sides—equal. Surface—furrowed throughout. Ridges—rounded. Pits—elongated. Ventral edge—thin. Dorsal edge—narrow. Tendency to split—slight. Color—near Strong Reddish-Orange, Plate 10R 6/12.

Use: Market; dessert.

Keeping quality: Good.

Shipping quality: Good.

General observations: Chilling requirement about the same as that of the variety known as "Tejon" (unpatented), but fruit is much firmer, larger and has a better blush color; chilling requirement much less than that of the variety known as "June Gold" (Plant Patent No. 1,884) which requires about 650 hours, and only slightly higher than that of "Early Amber" (Plant Patent No. 2,458) which requires only about 350 hours.

I claim:

1. A new and distinct variety of peach tree of the yellow-fleshed, freestone fruit-bearing type, substantially as herein shown and described, characterized particularly as to novelty by the unique combination of large, showy, pink colored flowers, good production of firm, yellow-fleshed fruit of the freestone type and of relatively large size and which developes a superior red blush on the skin, a relatively early fruit ripening habit corresponding to the very earliest of freestone varieties, while filling a void in the usual chain of ripening of established commercial varieties, a relatively low chilling requirement of about 400 to 450 hours at or below 45° F. for breaking dormancy and making the new variety adaptable to geographical areas where few peaches are grown commercially, and a superior fruit quality with respect to eating, keeping and shipping qualities.

No references cited.

ROBERT E. BAGWILL, *Primary Examiner.*